United States Patent [19]

Kim et al.

[11] 4,065,505

[45] Dec. 27, 1977

[54] OXIDATION PROCESS

[75] Inventors: Leo Kim; Timm E. Paxson; Sunny C. Tang, all of Houston, Tex.

[73] Assignee: Shell Oil Company, Houston, Tex.

[21] Appl. No.: 739,155

[22] Filed: Nov. 5, 1976

[51] Int. Cl.$^2$ ............................................. C07C 45/00
[52] U.S. Cl. ............................... 260/600 R; 260/599; 260/515 R; 260/465 D
[58] Field of Search ............................ 260/599, 600 R

[56] References Cited

U.S. PATENT DOCUMENTS

| | | | |
|---|---|---|---|
| 2,662,923 | 12/1953 | Reeder III | 260/599 X |
| 3,268,294 | 8/1966 | Roberts et al. | 260/599 X |
| 3,349,117 | 10/1967 | Selwitz et al. | 260/599 X |
| 3,637,830 | 1/1972 | Vanderwerff et al. | 260/599 X |

*Primary Examiner*—Bernard Helfin

[57] ABSTRACT

Meta-phenoxytoluene is oxidized by selenium dioxide in the presence of a dehydration agent to yield meta-phenoxy-benzaldehyde containing less than 250 ppm dissolved selenium at a selectivity based on the toluene of about 90% or better.

7 Claims, No Drawings

OXIDATION PROCESS

BACKGROUND OF THE INVENTION

1. Field of the Invention

The invention relates to a process for the oxidation of meta-phenoxytoluene by selenium dioxide in the presence of a dehydrating agent to produce meta-phenoxybenzaldehyde containing less than 250 ppm dissolved selenium. The invention relates to a process whereby the benzaldehyde can be recovered from the reaction mixture as the bisulfite addition product at the rate of 90%/hr. The invention further relates to a stoichiometric selenium dioxide oxidation of meta-phenoxytoluene to yield a selectivity of about 90% or greater based on the toluene.

2. Discussion of the Prior Art

The selective oxidation of an alkyl substituted aromatic compound to a benzaldehyde or phenylalkylketone presents a number of problems. In general, an attempt to oxidize alkyl aromatics selectively will lead to a mixture of alkyl aromatic alcohols, carbonyl compounds (aldehydes and ketones), carboxylic acids and phenols. Attempts to oxidize toluenes selectively to benzaldehydes are especially prone to produce benzoic acids because of the tendency of aldehydes to oxidize to the carboxylic acids. For example, the oxidation potentials to oxidize toluene to benzyl alcohol and benzyl alcohol to benzaldehyde are essentially the same as the oxidation potential to oxidize benzaldehyde to benzoic acid.

Contamination by alkyl oxidation products other than aldehyde is not the only problem. Ring oxidation is another direction an oxidation of toluene can take. While toluene is difficult to oxidize selectively to benzaldehyde, a ring substituted toluene offers additional problems. Those toluenes, having strong activating ortho-/paradirecting groups pose the problem of ring substitution. This is especially true in the case where the toluene is meta-substituted with the strong ortho-/para-directing phenoxy group since not only is the phenoxy group a strong ortho-/para-director but the methyl group is also an ortho-/para-director and the activated positions are common to both, i.e.

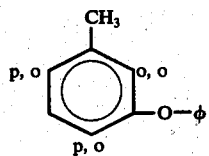

This makes the benzene ring sites designated p,o and o,o especially prone to the replacement of a hydrogen by a hydroxy group.

Selenium dioxide oxidations of organic compounds are known. Stoichiometric oxidation of alkyl substituted olefins are known to give the unsaturated carbonyl compound while stoichiometric oxidation of certain ketones are known to give the diketone. Early attempts to use a stoichiometric oxidation of toluene to benzaldehyde gave the expected mixture of products, i.e., 35% benzaldehyde and 10% benzoic acid c.f. Sultanov et al, Gen. Chem. (USSR), 16 2072 (1946). The best selectivity (based on toluene) are less than 90% of the benzaldehyde.

Selenium dioxide, oxygen and nitrogen dioxide have been employed to catalytically oxidize dimethylaryl compounds and it was reported that the main products under appropriate conditions were the dialdehydes, c.f. W. D. Vanderwerff et al U.S. Pat. No. 3,637,830. The selenium dioxide oxidation of alkyl aromatics whether stoichiometric or catalytic produce selenium compounds which are difficult to remove from the product and appear to interfere with the recovery of the aldehydes as the bisulfite addition product, e.g. less than 20% of the product will have precipitated as the adduct even after one hour.

The present invention is a process which reduces the amount of dissolved selenium in the final product, allows one to easily and quickly recover the aldehyde and in the case of the stoichiometric oxidation raises the selectivity (based on meta-phenoxytoluene going to m-phenoxybenzaldehyde) to about 90% or greater.

SUMMARY OF THE INVENTION

Meta-phenoxytoluene is stoichiometrically oxidized to meta-phenoxybenzaldehyde at a selectivity of about 90% or greater by contacting the toluene with selenium dioxide in the presence of a dehydrating agent at a temperature between about 150° and about 260° C in an inert solvent. Furthermore, the selenium dioxide oxidation may be carried out with only catalytic amounts of selenium dioxide in the presence of oxygen and nitric oxide. The meta-phenoxybenzaldehyde made in the presence of a dehydrating agent contain less than 250 ppm dissolved selenium and can be precipitated at the rate of 90%/hr to yield a product containing less than about 0.5 ppm dissolved selenium.

DESCRIPTION OF THE PREFERRED EMBODIMENTS

The invention relates to a process for producing substantially selenium-free meta-phenoxybenzaldehyde from meta-phenoxytoluene at high selectivity by contacting meta-phenoxytoluene with selenium oxide in the presence of a dehydrating agent. The invention relates to the selenium dioxide catalytic oxidation of meta-phenoxytoluene to substantially selenium-free meta-phenoxybenzaldehyde in the presence of oxygen and nitric oxide. The invention also relates to the selenium oxidation of meta-phenoxytoluene to substantially selenium-free meta-phenoxybenzaldehyde in the presence of a molecular sieve and further to the oxidation process where the benzaldehyde is recovered from the reactants by precipitating with $NaHSO_3$.

This invention is unique in that it achieves aldehyde selectivities which were not achievable before the use of dehydrating agents. Selectivities of as high as about 90%, preferably as high as about 95%, most preferably as high as about 98%. Meta-phenoxytoluene is preferably oxidized in an inert (at least stable to oxidation under the conditions used) organic solvent. The polarity of the solvent is between about 2.0 and about 20 as expressed in the dielectric constant, preferably between about 5 and about 15 and most preferably between about 8 and about 12. The boiling point of the solvent is preferably greater than about 120° C, most preferably greater than about 170° C. Examples of suitable solvents are fluorocarbons, halogenated benzenes, carbon tetrachloride and diphenylether. Preferred solvents are o-dichlorobenzene and carbon tetrachloride. The most preferred solvent is o-dichlorobenzene.

The initial concentration of meta-phenoxytoluene may vary over a wide range. Concentration of between about 2 weight percent and about 20 weight percent based on the combined amounts of meta-phenoxytoluene and solvent are preferred, and between 5 weight percent and 15 weight percent are most preferred.

The concentration of the selenium dioxide can vary from about 0.001 to about 4.0 equivalents depending on how the oxidation is carried out. If the oxidation is not catalytic then a preferred range is from about 0.1 to about 1.0 equivalents, most preferably between about 0.2 and about 1.0. If the reaction is carried out catalytically then a preferred range is from about 0.001 to about 0.5 equivalents, most preferably between about 0.01 and about 0.1.

The temperature of the oxidation may vary from about 150° C to about 260° C, preferably from about 190° C to about 260° C and most preferably from about 210° C to about 240° C.

In most instances the pressure of the reaction is above atmospheric and ranges from about 5 to about 300 psig, preferably from about 20 to about 200 psig and most preferably from about 50 to about 100 psig. The time of the oxidation may range from about 15 mins to about 4 hrs, preferably from about 0.5 hrs to about 2.5 hrs. The time of the reaction is somewhat dependent on the temperature and the desired conversion.

The oxidation is performed in the presence of a dehydrating or drying agent. The preferred types are the heterogeneous drying agents. Suitable drying agents are $MgSO_4$, $CaCl_2$, silicas, aluminas, alumina-silicates and molecular sieves. The preferred drying agents are the molecular sieves particularly the A type. Suitable amounts of drying agent range from about 0.1 to about 10 weight percent based on the total amount of reactants and solvent, preferably between about 0.5 to about 5 weight percent.

The presence of the drying agent during the stoichiometric oxidation reduces the dissolved selenium in the product to less than 1000 ppm, even less than 800 ppm and in some cases less than 700 ppm and reduces the dissolved selenium in a catalytic oxidation to less than about 500 ppm, even less than 250 ppm and in some cases less than 10 ppm. When the drying agent is used in the stoichiometric oxidation it increases the selectivity dramatically. This is not true in the catalytic oxidation and, in fact, the selectivity is reduced. However, the ease of recovery of the aldehydes as the bisulfite adduct is greatly enhanced in both the stoichiometric and catalytic reaction. Without the drying agent as part of the reaction the precipitation of the aldehyde as the bisulfite adduct from the reaction product is less than about 40% per hour but with the use of the drying agent as part of the reaction, the precipitation of the adduct is greater than about 50% per hour, even greater than 60% per hour and in some cases greater than 90% per hour.

The catalytic reaction: is shown as the sum of a number of reactions

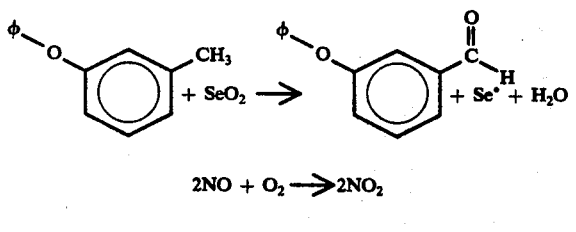

$$2NO + O_2 \rightarrow 2NO_2$$

$$Se° + 2NO_2 \rightarrow SeO_2 + 2NO$$

Net reaction:

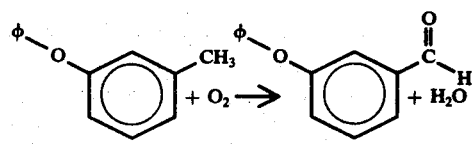

The catalytic mode gives somewhat lower selectivities (probably due to the presence of $NO_2$) but besides the obvious economic advantage in lower selenium use, the product when the reaction is carried out using a molecular sieve in the reaction medium has less than 10 ppm selenium (without using the $NaHSO_3$ step), an order of magnitude better than when the stoichiometric molecular sieve method is used.

Suitable levels of selenium dioxide for the catalytic oxidation are between 0.001 and about 0.5 preferably between .005 and about 0.25 and most preferably between 0.01 and about 0.1. Suitable partial pressures of NO at 250° C are between 0.1 and about 50 psi, preferably between 0.5 and about 20 and most preferably between 1 and about 10. Suitable partial pressure of oxygen are between 10 and about 100 psi, preferably between 20 and about 40. Air is the preferred source for the oxygen.

It is understood that one could start with Se° and $NO_2$ rather than $SeO_2$ + NO and $O_2$ but the invention would be the same as the present invention.

The presence of selenium in the benzaldehyde product could present a substantial environmental problem assuming the aldehyde would be used in products sold to the public. For that reason considerable effort has been devoted to carrying out the reaction in a mode which would produce a product with low selenium entrained therein and isolating this product in a manner which would even further minimize the entrained selenium. While fractional distillation, chromatography and/or crystallization may be used, the preferred method of isolating the aldehyde is to precipitate it with $NaHSO_3$ and wash with an oxygenated organic solvent such as methanol. When this isolation process is carried out on an aldehyde product which was made by a process not carried out in the presence of a molecular sieve, the precipitation is slow, for example, less than about 50% is precipitated in one hour, but when the $NaHSO_3$ is used on product made in the presence of a molecular sieve, greater than about 90% of the aldehyde is precipitated in an hour.

Suitable methods of recovering the neat aldehyde from its $NaHSO_3$ adduct involve mixing the adduct with water followed by separating the organic layer either by steam distillation, decanting the organic layer or extracting with a solvent in which the aldehyde is soluble, drying, and selectively distilling.

The use of the $NaHSO_3$ isolation step, with a catalytic oxidation embodiment run in the presence of a molecular sieve, reduces the selenium content of the aldehyde product to less than about 1 ppm.

Suitable quantities of $NaHSO_3$ useful in the isolation are between 1 and about 20 equivalents, preferably between 2 and about 15 and most preferably between 5 and about 10.

One particularly attractive use for the aldehyde made by this process is in the preparation of a valuable class of insecticides, the pyrethroids, as illustrated below: the meta-phenoxybenzaldehyde is used:

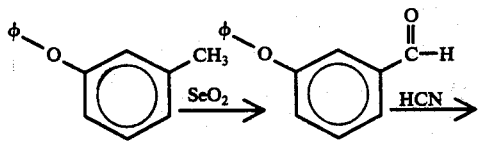

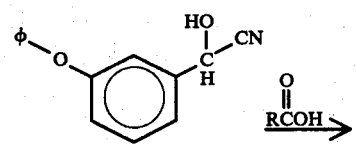

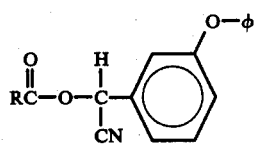

The following illustrative embodiments are presented to illustrate the invention and should not be taken as limiting the scope in any way.

ILLUSTRATIVE EMBODIMENT I

The majority of the reactions were carried out in Fisher-Porter vessels. The reactants were mixed initially in the vessel, and rapidly brought to the desired temperature with stirring provided magnetically. For SeO$_2$ oxidation reactions above 240°, an 80-ml glass-lined autoclave reactor with an internal thermowell was used.

A typical experimental procedure for SeO$_2$ oxidation of MPT is given bleow:

Experiment 1322-115

2.5g (13.6 mmol) of meta-phenoxytoluene, MPT, 0.755g (6.8 mmole) of SeO$_2$, 0.59g of 4A molecular sieve (dried at 300° for 1.5 hrs), and 22.5 ml of o-dichlorobenzene (reagent grade) were put in a 4-oz Fisher-Porter reactor with a Teflon ® stirring bar. The reaction mixture was then sealed, and purged with 3 × 50 psi of N$_2$ by repeated addition and venting. The chamber was then pressurized to 60 psi of N$_2$. The temperaure was then rapidly brought up to 235° with an external heater; the temperature being monitored by a thermocouple taped to the outside of the reactor. The reaction mixture was then stirred for 1.0 hr at 235°, at the end of which time the heater was removed, and the reaction mixture allowed to cool to room temperature. The product reaction mixture was then filtered, and the filtrate analyzed by GLC.

The results of this reaction are given in Tables I, II and III and illustrate the increased selectivity of a stoichiometric reaction when done at less than about 1.0 equivalent.

TABLE I

OXIDATION OF m-PHENOXYTOLUENE AT STOICHIOMETRIC EQUIVALENT OF SeO$_2$ (F & P reactor, 2.51 g MPT in 22.5 ml of o-dichlorobenzene, 1.0 equivalent of SeO$_2$ to MPT)

| LR | T° C | Time (hr) | Initial Pressure (psi) | % Conv | % Sel (MPB)* |
|---|---|---|---|---|---|
| 1248-115 | 195 | 2.0 | 70 | 6.3 | 94.3 |
| 1322-83 | 210 | 1.0 | 100 | 51.4 | 77.0 |
| 1248-116 | 220 | 0.5 | 70 | 25.8 | 84.3 |
|  | 220 | 1.0 | 70 | 28.9 | 92.6 |
| 1248-121 | 220 | 1.5 | 70 | 55.0 | 92.0 |
|  | 220 | 1.0 | 70 | 54.9 | 87.7 |
|  | 220 | 1.5 | 70 | 84.5 | 85.3 |
|  | 220 | 2.0 | 70 | 98.6 | 90.4 |
| 1322-89 | 230 | 1.0 | 100 | 75.6 | 64.9 |
| 1322-87 | 245 | 0.25 | 100 | 75.2 | 62.9 |

*MPB = meta-phenoxybenzaldehyde

TABLE II

OXIDATION OF m-PHENOXYTOLUENE AT LESS THAN STOICHIOMETRIC QUANTITY OF SeO$_2$ (F & P reactor, 2.51 g MPT in 22.5 ml of o-dichlorobenzene)

| LR | Rel amount of SeO$_2$ to MPT | T° C | Time (hr) | Initial Pressure (psi) | % Conv. | % Sel to MPB | Se (ppm) |
|---|---|---|---|---|---|---|---|
| 1248-131$^a$ | 0.25 | 220 | 1.0 | 70 | 14.4 | 97.4 | 1500 |
| 1322-82 | 0.3 | 210 | 2.0 | 100 | 25.8 | 87.3 | — |
| 1248-133 | 0.3 | 220 | 0.75 | 70 | 18.7 | 95.7 | 4300 |
| 1322-107 | 0.3 | 220 | 1.0 | 70 | 23.5 | 98.3 | 2000 |
| 1322-98 | 0.3 | 220 | 1.0 | 100 | 29.8 | 92.0 | 1200 |
| 1248-122 | 0.5 | 220 | 1.0 | 70 | 33.7 | 88.5 | 2900 |
| 1248-126 | 0.5 | 220 | 1.0 | 70 | 34.6 | 94.7 | — |
|  | 0.5 | 220 | 2.0 | 70 | 41.6 | 94.7 | — |

$^a$Reaction done under H$_2$

TABLE III

OXIDATION OF m-PHENOXYTOLUENE AT GREATER THAN STOICHIOMETRIC QUANTITY OF SeO$_2$ (F & P reactor, 2.51 g MPT in 22.5 ml of o-dichlorobenzene)

| LR | Rel amount of SeO$_2$ to MPT | T° C | Time (hr) | Initial Pressure (psi) | % Conv | % Sel (MPB) |
|---|---|---|---|---|---|---|
| 1248-117 | 2.0 | 220 | 0.5 | 70 | 8.4 | 94.7 |
| 1322-80 | 4.0 | 210 | 2.0 | 100 | 86.0 | 50.9 |

ILLUSTRATIVE EMBODIMENT II

The reaction was carried out as in Illustrative Embodiment I but in the presence of various absorbent materials to reduce the presence of water produced in the oxidation. The results are given in Table IV.

TABLE IV

SeO$_2$ OXIDATION OF m-PHENOXYTOLUENE IN THE PRESENCE OF MOLECULAR SIEVE
(F & P reactor, 2.5 g MPT in 22.5 ml o-dichlorobenzene)

| LR | mol sieve | Relative amt of SeO$_2$ | T° C | Time (hr) | Pressure (psi) |
|---|---|---|---|---|---|
| 1248-134 | 3A | 0.3 | 220 | 1.0 | 70 |
| 1315-76 | 3A | 0.5 | 240 | 2.0 | 75 |
| 1322-141 | 3A | 1.0 | 240 | 2.0 | 75 |
| 1322-113 | 4A | 1.0 | 220 | 1.0 | 60 |
|  | 4A | 1.0 | 220 | 2.0 | 60 |

TABLE IV-continued
SeO₂ OXIDATION OF m-PHENOXYTOLUENE IN THE PRESENCE OF MOLECULAR SIEVE
(F & P reactor, 2.5 g MPT in 22.5 ml o-dichlorobenzene)

| 1322-115 | 4A | 0.5 | 235 | 1.0 | 60 |
|---|---|---|---|---|---|
|  | 4A | 0.5 | 235 | 2.0 | 60 |
| 1322-132 | 4A | 0.5 | 240 | 1.0 | 60 |
|  | 4A | 0.5 | 240 | 2.0 | 60 |
| 1322-118 | 4A | 0.5 | 260 | 1.0 | 300 |
| 1322-122 | 4A | 0.5 | 270 | 1.0 | 300 |
| 1322-120 | 4A | 0.5 | 310 | 1.0 | 300 |
| 1322-72 | 5A | 0.5 | 220 | 2.0 | 75 |
| 1315-73 | 5A | 0.3 | 220 | 1.5 | 75 |
| 1315-78 | Na Zeolon | 0.5 | 240 | 1.5 | 50 |
| 1322-121 | mordenite | 0.5 | 240 | 1.0 | 60 |
| 1322-134 | 4A | 0.5 | 240 | 1.5 | 60 |

| LR | % Conv | % Sel (MPB) | Se (ppm) | Color of Product | Remarks |
|---|---|---|---|---|---|
| 1248-134 | 14.4 | ~97 | 770 | a |  |
| 1315-76 | 29.3 | 99.4 | 610 | a |  |
| 1322-141 | 47.2 | >99 | 610 | a |  |
| 1322-113 | 18.4 | 99.2 | — | a |  |
|  | 21.4 | 98.8 | 410 | a |  |
| 1322-115 | 24.6 | 98.9 | 610 | a |  |
|  | 24.6 | 98.8 | 610 | a |  |
| 1322-132 | 19.6 | >99 | 240 | a | twice usual amount of mol sieve |
|  | 20.6 | 99.3 | 310 | a | twice usual amount of mol sieve |
| 1322-118 | 24.3 | 99.0 | 460 | a | Autoclave reactor |
| 1322-122 | 7.0 | >99 | 150 | b | Autoclave reactor |
| 1322-120 | 18.2 | 44.9 | — | c | Autoclave reactor |
| 1322-72 | 10.2 | >99 | — | a |  |
| 1315-73 | 9.0 | >98 | — | a |  |
| 1315-78 | 42.8 | 83.9 | 6300 | c |  |
| 1322-121 | 22.6 | 83.3 | 4800 | b |  |
| 1322-134 | 1.93 | 89.6 | 91 | c | Solvent: ethylene diacetate | a Light yellow
b Light brown
c Dark brown

ILLUSTRATIVE EMBODIMENT III

The catalytic reactions were carried out as indicated in Illustrative Embodiment I, except that NO and $O_2$ were added at room temperature, with heating commencing after equilibrium. The results are given in Table V.

TABLE V
CATALYTIC OXIDATION REACTION OF m-PHENOXYTOLUENE
(F & P reactor, 2.5g MPT in 22.5 ml o-dichlorobenzene, 35 psi $O_2$, 220°, 1.5 hr)

| LR | Relative amt of Oxidant to MPT | NO (mmol) | % Conv |
|---|---|---|---|
| 1248-136[a] | SeO₂ | 0.01 | 1.6 | 12.5 |
| 1248-137[a] | SeO₂ | 0.01 | 1.6 | 5.3 |
| 1248-138[a] | SeO₂ | 0.1 | 1.6 | 18.6 |
| 1314-81[a] | SeO₂ | 0.01 | 14 | 21.5 |

| LR | % Sel (MPB) | Mol sieves | Se (ppm) | Remarks |
|---|---|---|---|---|
| 1248-136[a] | 85.4 | none | 153 | — |
| 1248-137[a] | 69.9 | 3A | 8 | — |
| 1248-138[a] | 85.2 | 3A | 214 | temp = 240° |
| 1314-81[a] | 47.3 | none | 122 | time = 1 hr, much nitration, see mol sieve attrition |

ILLUSTRATIVE EMBODIMENT IV

The NaHSO₃ precipitation experiments were performed by adding to a known amount of product solution the appropriate quantities of NaHSO₃ (solid), methanol and water. The mixture was then stirred magnetically for the given amount of time, then filtered. The solid was then dissolved in aqueous acid, and then extracted with dichloromethane. The pure aldehyde was recovered by the evaporation of the dichloromethane. The results are given in Tables VI and VII.

TABLE VI
SODIUM BISULFITE PRECIPITATION OF SeO₂ OXIDATION REACTIONS

| LR | Sample (ml) | Remark |
|---|---|---|
| 1248-119A | 10 | — |
| 1322-88 | 10 | — |
| 1248-119B | 10 | reduced to dryness |
| 1248-119E | 10 | reduced to dryness, washed with 0.1 N Na₂CO₃ |
| 1248-112 | 3 | Rxn solution passed through acidic alumina |
| 1322-98 | 3 | Rxn solution passed through acidic alumina |
| 1322-126 | 6 | Sample soln from mol sieve expt |
| 1322-131 | 21 | Sample soln from mol sieve expt |

| LR | NaHSO₃ (g) | Methanol (g) | H₂O (ml) | Time | %MPB Precipitated |
|---|---|---|---|---|---|
| 1248-119A | 2.5 | 10 | 0.28 | 0.5 hr | 0 |
|  |  |  |  | 1.0 hr | 16.1 |
|  |  |  |  | overnight | 81.3 |
| 1322-88 | 9.0 | 3 | 0.1 | overnight | 97 |
| 1248-119B | 1.2 | 5 | 0.2 | 0.5 hr | 15.3 |
|  |  |  |  | overnight | 85.2 |
| 1248-119E | 1.2 | 5 | 0.2 | overnight | 78.8 |
| 1248-112 | 2 | 7 | 0.3 | 1.0 hr | 63.6 |
| 1322-98 | 28 | 48 | 0.5 | 1.5 hr | 40.0 |
|  |  |  |  | 3.5 hr | 69.5 |
|  |  |  |  | overnight | 66.8 |
| 1322-126 | 4 | 14 | 0.2 | 1.0 hr | 87.0 |
| 1322-131 | 14 | 49 | 0.4 | 1.0 hr | 83.0 |

TABLE VII
SELENIUM ANALYSES FROM SODIUM BISULFITE WORKUPS

| 1322-131 Procedure | ppm Se |
|---|---|
| Starting o-dichlorobenzene (o-DCB) | 410 |
| NaHSO₃ treated, filtered; filtrate | 250 |
| NaHSO₃ washed with MeOH; NaHSO₃ | 5 |

TABLE VII-continued
SELENIUM ANALYSES FROM SODIUM BISULFITE WORKUPS

| | |
|---|---|
| The MeOH wash | 2.9 |
| NaHSO$_3$ dissolved in 0.1 N HCl | 1.0 |
| Extract aqueous layer with CH$_2$Cl$_2$; CH$_2$Cl$_2$ | <1.0 |
| 1322-126 Procedure | ppm Se |
| Starting o-DCB | 600 |
| NaHSO$_3$ treated, filtered; filtrate | 79 |
| NaHSO$_3$, unwashed | 600 |
| NaHSO$_3$ dissolved in H$_2$O, extract with CH$_2$Cl$_2$; CH$_2$Cl$_2$ | 170 |
| Aqueous layer after extraction | .8 |
| Acidified aqueous layer;extract with CH$_2$Cl$_2$; CH$_2$Cl$_2$ | .3 |

We claim as our invention:

1. In the process of oxidizing meta-phenoxytoluene selectively to meta-phenoxybenzaldehyde using selenium dioxide in the presence of an inert organic solvent at a temperature between about 150° C and about 260° C and at a pressure from about 5 to about 300 psig the improvement which comprises carrying out the reaction in the presence of a drying agent selected from the group consisting of MgSO$_4$, CaCl$_2$, silicas, aluminas, alumina-silicates and molecular sieves.

2. The process of claim 1 where the drying agent is present in an amount between about 0.1 and about 10 weight percent based on the total reactants and solvent.

3. The process of claim 2 where the drying agent is a type-A molecular sieve.

4. The process of claim 3 where the selenium dioxide is present in an amount between 0.5 to 1.0 equivalent, the selectivity is greater than about 98% based on meta-phenoxytoluene, and the meta-phenoxybenzaldehyde has a dissolved selenium content of less than 1000 ppm.

5. The process of claim 4 where the meta-phenoxybenzaldehyde is isolated by precipitating as the bisulfite adduct at the rate of at least 50% per hour by the addition of about 5 to about 10 equivalents, based on meta-phenoxybenzaldehyde, of NaHSO$_3$, said precipitate having less than about 0.5 ppm Se.

6. The process of claim 3 where the selenium dioxide is present in a catalytic amount together with NO and O$_2$ and the meta-phenoxybenzaldehyde contains less than about 10 ppm dissolved Se.

7. The process of claim 6 where the meta-phenoxybenzaldehyde is isolated by precipitating as the bisulfite adduct at a rate of at least 50% per hour by the addition of about 5 to about 10 equivalents, based on meta-phenoxybenzaldehyde, of NaHSO$_3$, said precipitate containing less than about 1 ppm selenium.

* * * * *